United States Patent
Liu et al.

(10) Patent No.: US 11,123,718 B2
(45) Date of Patent: Sep. 21, 2021

(54) OXOVANADIUM PHOSPHATE CATALYST, AND PREPARATION METHOD AND APPLICATION THEREFOR

(71) Applicant: INSTITUTE OF PROCESS ENGINEERING, CHINESE ACADEMY OF SCIENCES, Haidian District (CN)

(72) Inventors: Ruixia Liu, Beijing (CN); Bin He, Beijing (CN); Ruirui Zhang, Beijing (CN); Hongguo Tang, Beijing (CN); Suojiang Zhang, Beijing (CN)

(73) Assignee: INSTITUTE OF PROCESS ENGINEERING, CHINESE ACADEMY OF SCIENCES, Haidian District (CN)

( * ) Notice: Subject to any disclaimer, the term of this patent is extended or adjusted under 35 U.S.C. 154(b) by 0 days.

(21) Appl. No.: 16/961,029

(22) PCT Filed: Mar. 1, 2018

(86) PCT No.: PCT/CN2018/077705
§ 371 (c)(1),
(2) Date: Jul. 9, 2020

(87) PCT Pub. No.: WO2019/153387
PCT Pub. Date: Aug. 15, 2019

(65) Prior Publication Data
US 2020/0368730 A1 Nov. 26, 2020

(30) Foreign Application Priority Data
Feb. 9, 2018 (CN) .......................... 201810136362.1

(51) Int. Cl.
| | | |
|---|---|---|
| *B01J 27/198* | (2006.01) | |
| *B01J 27/199* | (2006.01) | |
| *B01J 37/04* | (2006.01) | |
| *B01J 37/08* | (2006.01) | |
| *C01B 25/37* | (2006.01) | |
| *C07D 307/60* | (2006.01) | |

(52) U.S. Cl.
CPC .......... *B01J 27/198* (2013.01); *B01J 27/199* (2013.01); *B01J 37/04* (2013.01); *B01J 37/088* (2013.01); *C01B 25/372* (2013.01); *C07D 307/60* (2013.01); *C01P 2004/03* (2013.01)

(58) Field of Classification Search
None
See application file for complete search history.

(56) References Cited

U.S. PATENT DOCUMENTS

2013/0102455 A1  4/2013  Haddad et al.

FOREIGN PATENT DOCUMENTS

| CN | 103551175 | | 2/2014 | |
|---|---|---|---|---|
| CN | 103551175 A | * | 2/2014 | ............ B01J 27/198 |
| CN | 103769181 | | 5/2014 | |
| CN | 103769181 A | * | 5/2014 | ............ B01J 27/198 |
| CN | 105921161 | | 9/2016 | |
| CN | 105921161 A | * | 9/2016 | ............ B01J 27/198 |
| CN | 106540729 | | 3/2017 | |
| CN | 106540729 A | * | 3/2017 | ............ B01J 27/198 |

OTHER PUBLICATIONS

International Search Report for PCT/CN2018/077705 dated Nov. 9, 2018.
Li, Guixian et al., Ionothermal Synthesis of Amorphous Vanadium Phosphate Catalyst in Eutectic Mixture for the Oxidation Reaction, Journal of Molecular Catalysis (China), vol. 28, No. 2, Apr. 30, 2014, pp. 105-111.
Office Action in CN201810136362.1 dated Feb. 27, 2020.

* cited by examiner

*Primary Examiner* — Brian J Davis
(74) *Attorney, Agent, or Firm* — Woodard, Emhardt, Henry, Reeves & Wagner, LLP

(57) ABSTRACT

Provided are an oxovanadium phosphate catalyst, and a preparation method and an application therefor. The method includes: 1) mixing and reacting a vanadium source, a choline chloride-organic carboxylic acid eutectic solvent, and alcohol; 2) mixing the obtained reaction product with a phosphorus source, raising the temperature to a temperature higher than the melting point of the eutectic solvent, and continuing the reaction to obtain an oxovanadium phosphate precursor; and 3) calcining to obtain the oxovanadium phosphate catalyst. The alcohol is: benzyl alcohol or a mixture of $C_3$-$C_8$ monohydric alcohol and benzyl alcohol. The present method uses a green and inexpensive eutectic solvent to strengthen the preparation of oxovanadium phosphate catalyst, avoids the disadvantages of the prior art, and overcoming the problems of low yield and poor selectivity when used in a reaction to prepare maleic anhydride by catalytic n-butane selective oxidisation.

20 Claims, 3 Drawing Sheets

OXOVANADIUM PHOSPHATE CATALYST, AND PREPARATION METHOD AND APPLICATION THEREFOR

TECHNICAL FIELD

The present application belongs to the field of chemical catalysis, and relates to a vanadyl phosphate catalyst, a method for preparing the same, and a use thereof.

BACKGROUND

A vanadyl phosphate catalyst (also referred to as a vanadium phosphorus oxide (VPO) catalyst) is a complex metal oxide catalyst composed of three elements of V, P, and O. Due to its special structure, the vanadyl phosphate catalyst is capable of selective oxidation of butane into maleic anhydride, and is currently the only catalyst to effect catalysis of this reaction. The catalyst is very complex in crystal phase composition, and has many crystal phases with various properties and compositions, which include $VOPO_4 \cdot 2H_2O$, $\alpha_I$-$VOPO_4$, $\alpha_{II}$-$VOPO_4$, $\beta$-$VOPO_4$, $\gamma$-$VOPO_4$, $VOHPO_4 \cdot 0.5H_2O$, $(VO)_2P_2O_7$, etc. reported in the literature. Varing crystal phases will affect an acid strength, micro-morphology, and the like of the VPO catalyst, which will affect a conversion rate an d selectivity of the reaction.

Vanadium phosphorus oxide (VPO) catalyst is typically produced by synthesis of a precursor using an aqueous or organic phase method, followed by filtration, drying, calcination activation and shaping. Most of early catalysts were prepared by the aqueous phase method. At present, the VPO catalysts for industry application all over the world are prepared by the organic phase method. However, the catalysts prepared by this method still have the problems of a small specific surface area, poor selectivity, and easy overoxidation. Current researches mainly focus on improving the performance of the catalysts by adding or impregnating with various metal and rare earth auxiliaries during or after the synthesis. However, this method greatly increases costs of the catalysts due to the addition of metal and rare earth elements, nitrogen oxides will be produced in the reaction process, and metal elements will be lost during the service of the catalysts, resulting in pollution and degraded performance of the catalysts.

SUMMARY

In view of the above-mentioned problems in the prior art, the present application aims to provide a vanadyl phosphate catalyst, a method for preparing the same, and a use thereof. The method of the present application adopts a cheap, non-toxic deep eutectic solvent to assist in the synthesis of the vanadyl phosphate catalyst, may be an environmentally friendly way of preparing the vanadyl phosphate catalyst, and can overcome the disadvantages of secondary pollution, high costs, and a complex preparation process of a traditional way of improving its performance which depends on a precious metal. A use of the catalyst for catalyzing the selective oxidation of n-butane to maleic anhydride overcomes the problems such as low yield, low catalyst selectivity, low conversion rate, auxiliary element losses, and high costs of the selective oxidation of n-butane to maleic anhydride in the prior art.

To achieve the object, the present application adopts the technical solutions described below.

In a first aspect, the present application provides a method for preparing a vanadyl phosphate catalyst. The method includes the following steps:

(1) mixing a vanadium source with a deep eutectic solvent and alcohol to obtain a mixture, and reacting the mixture;

(2) mixing a reaction product obtained in step (1) with a phosphorus source, raising the temperature to a temperature higher than a melting point of the deep eutectic solvent, and continuing a reaction to obtain a vanadyl phosphate precursor; and (3) carrying out calcination to obtain the vanadyl phosphate catalyst.

The deep eutectic solvent is a deep eutectic solvent formed by choline chloride and an organic carboxylic acid (simply referred to as choline chloride-organic carboxylic acid deep eutectic solvent).

The alcohol is benzyl alcohol or a mixture of $C_3$-$C_8$ monohydric alcohol and benzyl alcohol.

In the present application, a phosphorus-containing deep eutectic solvent may also be used as the phosphorus source.

In the present application, a heating reaction is carried out within a range higher than the melting point of the deep eutectic solvent, which can maintain the good fluidity of the deep eutectic solvent and a high boiling state of the system to ensure a rapid progress of the reaction. The deep eutectic solvent formed by choline chloride and the organic carboxylic acid can form a complex with vanadium, regulate a concentration of the vanadium source in the system, and control a crystal growth process, thereby giving a catalyst with better crystallinity.

"$C_3$-$C_8$ monohydric alcohol" in the present application refers to any one or a combination of at least two of monohydric alcohol with 3-8 carbon atoms, for example, may be propanol, isobutanol, n-butanol, pentanol, hexanol, heptanol, octanol, a combination of propanol and isobutanol, a combination of propanol and pentanol, a combination of n-butanol and hexanol, a combination of n-butanol and octanol, a combination of propanol, isobutanol, pentanol, and octanol, etc., preferably isobutanol.

In the present application, the deep eutectic solvent is formed from choline chloride and the organic carboxylic acid by a existing method, and the preparation can be done by those skilled in the art by reference to a method disclosed in the prior art, for example as follows:

a hydrogen bond donor (such as the organic carboxylic acid) and a hydrogen bond acceptor (such as choline chloride) in the deep eutectic solvent are added to a reaction vessel at a molar ratio of 0.5-2:0.5-1, mixed, stirred, and heated to 50-100° C. until a uniform, transparent mixture is formed.

Preferred solutions of the present application are set forth below and not intended to limit the solutions of the present application. Technical objects and beneficial effects of the present application can be better achieved through the preferred solutions set forth below.

Preferably, the organic carboxylic acid includes any one or a combination of at least two of malonic acid, oxalic acid, and tartaric acid (the formed deep eutectic solvent is, for example, choline chloride-malonic acid, choline chloride-oxalic acid, and choline chloride-tartaric acid, etc.), but is not limited to the above-listed organic carboxylic acids. Other organic carboxylic acids commonly used in the art which may react with choline chloride to form the choline chloride-organic carboxylic acid deep eutectic solvent and achieve the same effects may also be used in the present application. Oxalic acid is preferred.

Preferably, the alcohol is the mixture of $C_3$-$C_8$ monohydric alcohol and benzyl alcohol, preferably a mixture of isobutanol and benzyl alcohol.

Preferably, when the alcohol is benzyl alcohol, a volume ratio of the deep eutectic solvent to benzyl alcohol is (0.15-0.25):1, for example, 0.15:1, 0.17:1, 0.18:1, 0.20:1, 0.22:1, or 0.25:1, etc.

Alternatively, when the alcohol is the mixture of $C_3$-$C_8$ monohydric alcohol and benzyl alcohol, a volume ratio of the deep eutectic solvent, $C_3$-$C_8$ monohydric alcohol, and benzyl alcohol is (0.15-0.25):(3-5):1, for example, 0.15:3:1, 0.18:3:1, 0.2:3:1, 0.2:4:1, 0.2:4.5:1, 0.2:4.7:1, 0.2:5:1, 0.25:3:1, 0.25:4:1, or 0.25:5:1, etc.

As a preferred solution of the method of the present application, the method further includes adding either or both of a metal oxide and a metal salt while adding the deep eutectic solvent.

Preferably, a metal element in the metal oxide or the metal salt is independently selected from any one or a combination of at least two of Fe, Cu, Co, Mn, Ni, Zr, Zn, Ce, and Mo, preferably Zr and Mo.

Preferably, an atomic molar ratio of the metal element to a vanadium element in the vanadium source is 0.0005-0.035, for example, 0.0005, 0.0008, 0.001, 0.002, 0.003, 0.005, 0.01, 0.015, 0.02, 0.03, or 0.035, etc.

Preferably, a mass ratio of the vanadium source to the deep eutectic solvent is (50-10):1, for example, 50:1, 45:1, 40:1, 30:1, 25:1, 20:1, 15:1, or 10:1, etc., preferably (20-30):1. If the mass ratio is less than 10:1 and the deep eutectic solvent is added in too high an amount, a crystal form and acidity of the catalyst will come across large changes, resulting in a decrease in selectivity. If the mass ratio is larger than 50:1, the deep eutectic solvent is low in content and cannot enhance the catalyst.

Preferably, in the mixture, the vanadium source has a concentration of 0.02 g/mL to 0.12 g/mL, for example, 0.02 g/mL, 0.04 g/mL, 0.06 g/mL, 0.07 g/mL, 0.08 g/mL, 0.09 g/mL, 0.1 g/mL, or 0.12 g/mL, etc. If the concentration is lower than 0.02 g/mL, a vanadium-phosphorus ratio decreases, and an active crystal phase cannot be formed. If the concentration is higher than 0.12 g/mL, a large number of impurity phases are formed, resulting in the decrease in selectivity.

Preferably, a molar ratio of phosphorus in the phosphorus source to vanadium in the vanadium source is (0.8-1.5):1, for example, 0.8:1, 0.9:1, 1:1, 1.1:1, 1.2:1, 1.3:1, 1.4:1, or 1.5:1, etc., preferably (0.9-1.2):1. If the molar ratio is less than 0.8:1, phosphorus in the catalytic system is lost faster, and the catalyst has a reduced life. If the molar ratio is larger than 1.5:1, a large number of impurity phases are formed.

As a preferred solution of the method of the present application, a manner for the mixing in step (1) is placing the vanadium source in a vessel, and then adding a mixed solution of the deep eutectic solvent and the alcohol.

Preferably, the vanadium source in step (1) includes any one or a combination of at least two of a vanadium salt and a vanadium oxide, preferably includes any one or a combination of at least two of $V_2O_5$, $NH_4VO_3$, $V_2O_4$, and $V_2O_3$. But it is not limited the above-listed vanadium sources, and other vanadium sources commonly used in the art and capable of achieving the same effects may be used in the present application. $V_2O_5$ is preferred.

Preferably, a temperature for the reaction in step (1) is 100° C. to 180° C., for example, 100° C., 110° C., 120° C., 130° C., 140° C., 145° C., 150° C., 155° C., 165° C., 170° C., or 180° C., etc., preferably 130° C. to 140° C.

Preferably, a duration for the reaction in step (1) is 2 h to 8 h, for example, 2 h, 3 h, 4 h, 5 h, 5.5 h, 6 h, 7 h, or 8 h, etc., preferably, 3 h to 5 h.

Preferably, after the reaction in step (1), the reaction product is cooled to 30° C. to 80° C., for example, 30° C., 35° C., 40° C., 50° C., 60° C., 70° C., or 80° C., etc.

Preferably, the phosphorus source in step (2) includes any one or a combination of at least two of a phosphoric acid, a phosphate, and a phosphorus oxide, preferably includes 85% of any one or a combination of at least two of a phosphoric acid (such as a commercially available concentrated phosphoric acid), the phosphate, and the phosphorus oxide in mass fraction, further preferably includes 85% of any one or a combination of at least two of the phosphoric acid, $(NH_4)_3PO_4$, $(NH_4)_2HPO_4$, $NH_4H_2PO_4$, $P_2O_5$, and $P_2O_3$ in mass fraction. But it is not limited the above-listed phosphorus sources, and other phosphorus sources commonly used in the art and capable of achieving the same effects may be used in the present application.

Preferably, in step (2), the temperature is raised to 35° C. to 200° C. higher than the melting point of the deep eutectic solvent, for example, 35° C., 40° C., 42° C., 45° C., 50° C., 55° C., 60° C., 65° C., 70° C., 75° C., 85° C., 100° C., 110° C., 125° C., 150° C., 175° C., or 200° C. higher than the melting point.

Preferably, in step (2), the temperature is raised to 100° C. to 200° C., for example, 100° C., 120° C., 130° C., 140° C., 150° C., 160° C., 170° C., 180° C., or 200° C., etc.

Preferably, in step (2), the reaction is continued for a duration of 10 h to 24 h, for example, 10 h, 12 h, 13 h, 15 h, 17 h, 18 h, 20 h, 21 h, 22 h, 23 h, or 24 h, etc.

Preferably, after the continued reaction in step (2) is finished, steps of filtering, washing, and drying are performed.

Preferably, in step (3), a calcination atmosphere is a nitrogen atmosphere, a mixed atmosphere of n-butane and air, or a mixed atmosphere of n-butane, oxygen, and nitrogen.

Preferably, in the mixed atmosphere of n-butane and air, a volume ratio of n-butane to the air is (0.8-1.8):100, for example, 0.8:100, 1:100, 1.2:100, 1.5:100, or 1.8:100, etc.

Preferably, in the mixed atmosphere of n-butane, oxygen, and nitrogen, a volume ratio of n-butane, oxygen, and nitrogen is (0.8-1.8):(10-25):(75-85), for example, 0.8:10:75, 1:10:85, 1.5:10: 80, 1.8:10:75, 0.8:20:75, 1:20:80, 1.5:20:85, 1.8:25:75, or 1:20:85, etc.

Preferably, a temperature for the calcination in step (3) is 350° C. to 550° C., for example, 350° C., 360° C., 370° C., 380° C., 400° C., 420° C., 430° C., 450° C., 475° C., 500° C., 515° C., 530° C., or 550° C., etc.

Preferably, a duration for the calcination in step (3) is 10 h to 24 h, for example, 10 h, 12 h, 13.5 h, 15 h, 16 h, 18 h, 20 h, 22 h, or 24 h, etc.

In order to facilitate the evaluation of effects of the catalyst, the calcination step in the present application may be performed after the vanadyl phosphate precursor is formed, so that the calcined catalyst is directly used for the evaluation of the effects, or the vanadyl phosphate precursor may also be calcined, followed by forming, and then used for the evaluation of the effects of the catalyst.

As a further preferred solution of the method of the present application, the method includes the following steps:

(1) placing vanadium pentoxide in a vessel and then adding a deep eutectic solvent, isobutanol, and benzyl alcohol to be mixed with vanadium pentoxide to obtain a mixture, reacting the mixture at 130° C. to 140° C. for 3 h to 5 h, and then cooling the reaction product to 30-80° C.;

(2) adding a phosphorus source to the vessel, raising the temperature to 100° C. to 200° C., continuing a reaction for 10 h to 24 h, filtering, washing, and drying the resultant to obtain an vanadyl phosphate precursor; and (3) carrying out calcination at 350° C. to 550° C. for 10 h to 24 h in a nitrogen atmosphere, a mixed atmosphere of n-butane and air, or a mixed atmosphere of n-butane, oxygen, and nitrogen, to achieve in-situ activation so as to obtain the vanadyl phosphate catalyst.

The deep eutectic solvent is a deep eutectic solvent formed by choline chloride and an organic carboxylic acid.

A mass ratio of vanadium pentoxide to the deep eutectic solvent is (20-30):1.

A volume ratio of the deep eutectic solvent, isobutanol, and benzyl alcohol is (0.15-0.25): (3-5): 1.

In the mixture, vanadium pentoxide has a concentration of 0.02 g/mL to 0.12 g/mL.

A molar ratio of phosphorus in the phosphorus source to vanadium in the vanadium source is (0.9-1.2):1.

In a second aspect, the present application provides a vanadyl phosphate catalyst prepared by the method described in the first aspect, where the vanadyl phosphate catalyst has a specific surface area of 25 $m^2/g$ to 35 $m^2/g$.

Preferably, the vanadyl phosphate catalyst has a specific surface area of 29 $m^2/g$.

In a third aspect, the present application provides a use of the vanadyl phosphate catalyst described in the second aspect for selective oxidation of n-butane to maleic anhydride. Preferably, reaction conditions for the selective oxidation of n-butane to maleic anhydride include a reaction temperature of 400° C. to 550° C., a pressure of 0.1 MPa to 0.3 MPa, a space velocity of a mixed gas of n-butane of 1000 $h^{-1}$ to 2500 $h^{-1}$, and an n-butane concentration of 1.3 wt % to 1.8 wt %.

Compared with the existing technologies, the present application has beneficial effects described below.

(1) The deep eutectic solvent used in the present application is simple to synthesize, non-toxic, inexpensive, and biodegradable, and may be prepared in large quantities.

(2) The method of the present application is a method for preparing the vanadyl phosphate catalyst enhanced by the deep eutectic solvent. In the method, the deep eutectic solvent serves as a structure directing agent and a crystal plane directing agent, a solvent as well as a promoter, and modifies properties of the catalyst during the synthesis. Through a process design of the present application, the deep eutectic solvent plays the above various synergistic enhancement effects, so that the selectivity and a conversion rate of the VPO catalyst enhanced by the deep eutectic solvent are greatly improved, achieving effects which are equivalent to or superior to those of the existing technologies in which a metal promoter is doped.

(3) Compared with a traditional metal impregnation method, the method of the present application has simplified preparation procedures of the catalyst, less costs and simple operations, and is suitable for industrial production.

(4) The present application adopts the deep eutectic solvent to enhance the activity and the selectivity of the VPO catalyst, overcomes the disadvantages of a traditional method using a metal and rare earth element as a auxiliary such as the generation of nitrogen oxides in an addition process, high costs, and metal losses and secondary pollution in the service of the catalyst, complies with the development requirements of green chemistry. Moreover, both the selectivity and the conversion rate of the VPO catalyst enhanced by the deep eutectic solvent are greatly improved.

DETAILED DESCRIPTION

Figure 1:
FIG. 1 is a scanning electron micrograph of a vanadyl phosphate precursor obtained in step (2) in Example 1 of the present application.

Solutions of the present application are described more fully below through specific embodiments in conjunction with the drawings.

An embodiment of the present application provides a method for preparing a vanadyl phosphate catalyst. The method includes steps described below.

In S01 a vanadium source was placed in a vessel, a mixed solution of a deep eutectic solvent, isobutanol, and benzyl alcohol with a volume ratio of (0.15-0.25):(3-5):1 was added, the temperature was raised to 100° C. to 180° C. for a reaction of 2 h to 8 h, the resultant was then cooled to 30° C. to 80° C., a phosphorus source was added, the temperature was raised to 100° C. to 200° C. to continue a reaction for 10 h to 24 h, and a product was filtered, washed, and dried to obtain a vanadyl phosphate precursor, where a molar ratio of phosphorus in the phosphorus source to vanadium in the vanadium source was (0.8-1.5):1, the concentration of vanadium pentoxide in the mixed solution of isobutanol and benzyl alcohol was 0.02 g/mL to 0.12 g/mL, and a mass ratio of the vanadium source to the deep eutectic solvent was (50-10):1.

In S02, the vanadyl phosphate precursor was calcined at 350° C. to 550° C. for 10 h to 24 h to be activated, and cooled to obtain an activated vanadyl phosphate catalyst.

Specifically, the vanadium source is a vanadium salt or a vanadium oxide, where the vanadium salt was $NH_4VO_3$, and the vanadium oxide was any one or a combination of at least two of $V_2O_5$, $V_2O_4$, and $V_2O_3$; and the phosphorus source was at least one of a phosphoric acid, a phosphate, or a phosphorus oxide, where the phosphate was at least one of $(NH_4)_3PO_4$, $(NH_4)_2HPO_4$, or $NH_4H_2PO_4$, and the phosphorus oxide is $P_2O_5$ or $P_2O_3$. The selected deep eutectic solvent included any one or a combination of at least two of choline chloride-malonic acid, choline chloride-oxalic acid, and choline chloride-tartaric acid.

The calcination step in the present application may be performed after the vanadyl phosphate precursor was formed, so that the calcined catalyst may be directly used for the evaluation of the effects; or the vanadyl phosphate precursor may also be calcined, followed by forming, and then used for the evaluation of the effects of the catalyst.

An embodiment of the present application further provides a use of the vanadyl phosphate catalyst obtained by the above method for selective oxidation of n-butane to maleic anhydride.

An embodiment of the present application further provides a use of the vanadyl phosphate catalyst obtained by the above method for selective oxidation of n-butane to maleic anhydride.

Reaction conditions for preparing maleic anhydride with vanadium phosphorus oxides include a reaction temperature of 380° C. to 450° C., a normal pressure of 0.1 MPa to 0.5 MPa, a space velocity of a mixed gas of n-butane of 1000 $h^{-1}$ to 3500 $h^{-1}$, and an n-butane concentration of 1.0 wt % to 1.8 wt %.

The method for preparing an vanadyl phosphate catalyst is illustrated below through specific examples. Compounds in the following examples may be directly prepared according to existing methods, and of course, the compounds may also be directly purchased on the market in other examples, but it is not limited thereto.

EXAMPLE 1

An vanadyl phosphate catalyst was prepared as follows:

(1) 10 g of $V_2O_5$ were weighed and placed in a 250 mL three-neck flask, a mixed solution of 1 g of choline chloride-oxalic acid deep eutectic solvent, 80 mL of isobutanol, and 20 mL of benzyl alcohol was added, the mixture was mechanically stirred to be uniformly mixed and refluxed at 135° C. for 3 h, and then the temperature was decreased to 60° C.

(2) 7.53 mL of 85% $H_3PO_4$ were added dropwise slowly, and the temperature was raised to 135° C. for continued reflux for 16 h. A product was filtered and washed with absolute ethanol to obtain a blue precipitate which was dried in air for 24 h at 120° C. to obtain vanadyl phosphate catalyst precursor powder.

(3) The obtained vanadyl phosphate catalyst precursor powder was pressed at a pressure of 15 MPa and crushed, and 20-40 meshes of catalyst particles were sieved.

(4) The catalyst particles were heated from room temperature at a heating rate of 2° C./min in a mixed reaction atmosphere of n-butane/oxygen/nitrogen with a volume ratio of 1.5:17:81.5 to 430° C. and then activated in situ for 12 h to obtain the vanadyl phosphate catalyst.

Detection:

2.6 g of vanadyl phosphate catalyst were weighed and placed in a fixed-bed reactor with an inner diameter of 14 mm for catalyst performance evaluation. The vanadyl phosphate catalyst reacted with a feed gas whose composition was $C_4H_{10}/O_2/N2=1.4/19.5/79$ (v/v/v) at a reaction temperature of 420° C., a reaction pressure of 0.12 MPa, and a gas space velocity of 2000 $h^{-1}$. A reaction tail gas was analyzed online through gas chromatography to obtain results that a conversion rate of n-butane was 86.94%, the selectivity of maleic anhydride was 60.21%, and a yield of maleic anhydride was 55.24%.

Crystallographic data of the vanadyl phosphate precursor obtained in step (2) in Example 1 is listed in Table 1, and crystallographic data of the activated vanadyl phosphate catalyst obtained in step (4) in Example 1 is listed in Table 2.

EXAMPLE 2

A vanadyl phosphate catalyst was prepared as follows:

(1) 10 g of $V_2O_5$ were weighed and placed in a 250 mL three-neck flask, a mixed solution of 1 g of choline chloride-tartaric acid deep eutectic solvent, 80 mL of isobutanol, and 20 mL of benzyl alcohol was added, the mixture was mechanically stirred to be uniformly mixed and refluxed at 135° C. for 3 h, and then the temperature was decreased to 60° C.

(2) 7.53 mL of 85% $H_3PO_4$ were added dropwise slowly, and the temperature was raised to 135° C. for continued reflux for 16 h. A product was filtered and washed with absolute ethanol to obtain a dark blue precipitate which was dried in air for 24 h at 120° C. to obtain vanadyl phosphate catalyst precursor powder.

(3) The obtained vanadyl phosphate catalyst precursor powder was pressed at a pressure of 15 MPa and crushed, and 20-40 meshes of catalyst particles were sieved.

(4) The catalyst particles were heated from room temperature at a heating rate of 2° C./min in a mixed reaction atmosphere of n-butane/oxygen/nitrogen with a volume ratio of 1.5:17:81.5 to 430° C. and then activated in situ for 12 h to obtain the vanadyl phosphate catalyst.

Detection:

2.6 g of vanadyl phosphate catalyst were weighed and placed in a fixed-bed reactor with an inner diameter of 14 mm for catalyst performance evaluation. The vanadyl phosphate catalyst reacted with a feed gas whose composition was $C_4H_{10}/O_2/N_2=1.4/19.5/79$ (v/v/v) at a reaction temperature of 420° C., a reaction pressure of 0.12 MPa, and a gas space velocity of 2000 $h^{-1}$. A reaction tail gas was analyzed online through gas chromatography to obtain results that a conversion rate of n-butane was 88.46%, the selectivity of maleic anhydride was 58.57%, and a yield of maleic anhydride was 52.81%.

Crystallographic data of the vanadyl phosphate precursor obtained in step (2) in Example 2 is listed in Table 1, and crystallographic data of the activated vanadyl phosphate catalyst obtained in step (4) in Example 2 is listed in Table 2.

EXAMPLE 3

A vanadyl phosphate catalyst was prepared as follows:

(1) 10 g of $V_2O_5$ were weighed and placed in a 250 mL three-neck flask, a mixed solution of 1 g of choline chloride-malonic acid deep eutectic solvent, 80 mL of isobutanol, and 20 mL of benzyl alcohol was added, the mixture was mechanically stirred to be uniformly mixed and refluxed at 135° C. for 3 h, and then the temperature was decreased to 60° C.

(2) 7.53 mL of 85% $H_3PO_4$ were added dropwise slowly, and the temperature was raised to 135° C. for continued reflux for 16 h. A product was filtered and washed with absolute ethanol to obtain a blue precipitate which was dried in air for 24 h at 120° C. to obtain vanadyl phosphate catalyst precursor powder.

(3) The obtained vanadyl phosphate catalyst precursor powder was pressed at a pressure of 15 MPa and crushed, and 20-40 meshes of catalyst particles were sieved.

(4) The catalyst particles were heated from room temperature at a heating rate of 2° C./min in a mixed reaction atmosphere of n-butane/oxygen/nitrogen with a volume ratio of 1.5:17:81.5 to 430° C. and then activated in situ for 12 h to obtain the vanadyl phosphate catalyst.

Detection:

2.6 g of vanadyl phosphate catalyst were weighed and placed in a fixed-bed reactor with an inner diameter of 14 mm for catalyst performance evaluation. The vanadyl phosphate catalyst reacted with a feed gas whose composition was $C_4H_{10}/O_2/N_2$=1.4/19.5/79 (v/v/v) at a reaction temperature of 420° C., a reaction pressure of 0.12 MPa, and a gas space velocity of 2000 $h^{-1}$. A reaction tail gas was analyzed online through gas chromatography to obtain results that a conversion rate of n-butane was 94.31%, the selectivity of maleic anhydride was 56.27%, and a yield of maleic anhydride was 53.07%.

Crystallographic data of the vanadyl phosphate precursor obtained in step (3) in Example 3 is listed in Table 1, and crystallographic data of the activated vanadyl phosphate catalyst obtained in step (4) in Example 3 is listed in Table 2.

EXAMPLE 4

The preparation method and conditions were the same as those in Example 1, except for the following content:

Addition amounts of vanadium pentoxide, the choline chloride-tartaric acid deep eutectic solvent, isobutanol, benzyl alcohol, and the phosphoric acid were adjusted to 5 g, 1 g, 10 mL, 40 mL, and 3.77 mL, respectively.

A reflux condition in step (1) was adjusted to reflux at 100° C. for 8 h.

Step (2) was adjusted to raising the temperature to 150° C. for continued reflux for 12 h.

Step (4) was adjusted to being heated to 350° C. and being activated in situ for 24 h.

Detection was carried out by the same method under the same conditions as in Example 1. Detection results were that a conversion rate of n-butane was 92.31%, the selectivity of maleic anhydride was 51.27%, and a yield of maleic anhydride was 47.32%.

EXAMPLE 5

The preparation method and conditions were the same as those in Example 1, except for the following content:

Addition amounts of vanadium pentoxide, the choline chloride-tartaric acid deep eutectic solvent, isobutanol, benzyl alcohol, and the phosphoric acid were adjusted to 3 g, 1 g, 15 mL, 40 mL, and 2.26 mL, respectively.

A reflux condition in step (1) was adjusted to reflux for 5 h at 140° C.

Step (2) was adjusted to raising the temperature to 180° C. for continued reflux for 10 h.

Step (4) was adjusted to being heated to 550° C. and being activated in situ for 10 h.

Detection was carried out by the same method under the same conditions as in Example 1. Detection results were that a conversion rate of n-butane was 92.05%, the selectivity of maleic anhydride was 55.36%, and a yield of maleic anhydride was 50.96%.

EXAMPLE 6

The preparation method and conditions were the same as those in Example 1, except for the following content:

Addition amounts of vanadium pentoxide, the choline chloride-tartaric acid deep eutectic solvent, isobutanol, benzyl alcohol, and the phosphoric acid were adjusted to 1.5 g, 1 g, 15 mL, 35 mL, and 1.3 mL, respectively.

A reflux condition in step (1) was adjusted to reflux for 2 h at 170° C.

Step (2) was adjusted to raising the temperature to 160° C. for continued reflux for 15 h.

Step (4) was adjusted to being heated to 450° C. and being activated in situ for 18 h.

Detection was carried out by the same method under the same conditions as in Example 1. Detection results were that a conversion rate of n-butane was 93.02%, the selectivity of maleic anhydride was 54.17%, and a yield of maleic anhydride was 50.38%.

EXAMPLE 7

The preparation method and conditions were the same as those in Example 1, except for the following content:

Types and amounts of solvents added were adjusted. Addition amounts of vanadium pentoxide, the choline chloride-tartaric acid deep eutectic solvent, isobutanol, benzyl alcohol, and the phosphoric acid were 5 g, 1 g, 10 mL, 40 mL, and 3.77 mL, respectively.

A reflux condition in step (1) was adjusted to reflux for at 100° C. for 5.5 h.

Step (2) was adjusted to raising the temperature to 150° C. for continued reflux for 12 h.

Step (4) was adjusted to being heated to 350° C. and being activated in situ for 48 h.

Detection was carried out by the same method under the same conditions as in Example 1. Detection results were that a conversion rate of n-butane was 90.52%, the selectivity of maleic anhydride was 55.26%, and a yield of maleic anhydride was 50.02%.

EXAMPLE 8

A vanadyl phosphate catalyst was prepared as follows:

(1) 10 g of $V_2O_5$ were weighed and placed in a 250 mL three-neck flask, a mixed solution of 1 g of choline chloride-oxalic acid deep eutectic solvent, 80 mL of isobutanol, and 20 mL of benzyl alcohol was added, the mixture was mechanically stirred to be uniformly mixed and refluxed at 145° C. for 3.5 h, and then the temperature was decreased to 40° C.

(2) 7.53 mL of 85% $H_3PO_4$ were added dropwise slowly, and the temperature was raised to 165° C. for continued reflux for 14 h. A product was filtered and washed with absolute ethanol to obtain a blue precipitate which was dried in air for 18 h at 100° C. to obtain vanadyl phosphate catalyst precursor powder.

(3) The vanadyl phosphate catalyst precursor powder was heated from room temperature at a heating rate of 2° C./min in a mixed reaction atmosphere of n-butane/oxygen/nitrogen with a volume ratio of 1.5:17:81.5 to 475° C. and then activated in situ for 15 h to obtain the vanadyl phosphate catalyst.

(4) The obtained catalyst was pressed at a pressure of 15 MPa and crushed, and 20-40 meshes of catalyst particles were sieved.

Detection was carried out by the same method under the same conditions as in Example 1. Detection results were that a conversion rate of n-butane was 93.42%, the selectivity of maleic anhydride was 55.26%, and a yield of maleic anhydride was 51.62%.

COMPARATIVE EXAMPLE 1

10 g of $V_2O_5$ were weighed and placed in a 250 mL three-neck flask, a mixed solution of 80 mL of isobutanol and 20 mL of benzyl alcohol was added, the mixture was mechanically stirred to be uniformly mixed and refluxed at 135° C. for 3 h, and then the temperature was decreased to 60° C. 7.53 mL of 85% $H_3PO_4$ were added dropwise slowly, and the temperature was raised to 135° C. for continued reflux for 16 h. A product was filtered and washed with absolute ethanol to obtain a blue precipitate which was dried in air for 24 h at 120° C. to obtain vanadyl phosphate catalyst precursor powder. The obtained vanadyl phosphate catalyst precursor powder was pressed at a pressure of 15 MPa and crushed, and 20-40 meshes of catalyst particles were sieved. The catalyst particles were heated from room temperature at a heating rate of 2° C./min in a mixed reaction atmosphere of n-butane/oxygen/nitrogen with a volume ratio of 1.5:17: 81.5 to 430° C. and then activated in situ for 12 h to obtain the activated vanadyl phosphate catalyst.

2.6 g of activated catalyst were weighed and placed in a fixed-bed reactor with an inner diameter of 14 mm for catalyst performance evaluation. The activated catalyst reacted with a feed gas whose composition was $C_4H_{10}/O_2/N_2$=1.5/19.5/79 (v/v/v) at a reaction temperature of 420° C., a reaction pressure of 0.12 MPa, and a gas space velocity of 2000 $h^{-1}$. A reaction tail gas was analyzed online through gas chromatography to obtain results that a conversion rate of n-butane was 80.86%, the selectivity of maleic anhydride was 55.74%, and a yield of maleic anhydride was 45.07%.

Figure 2:
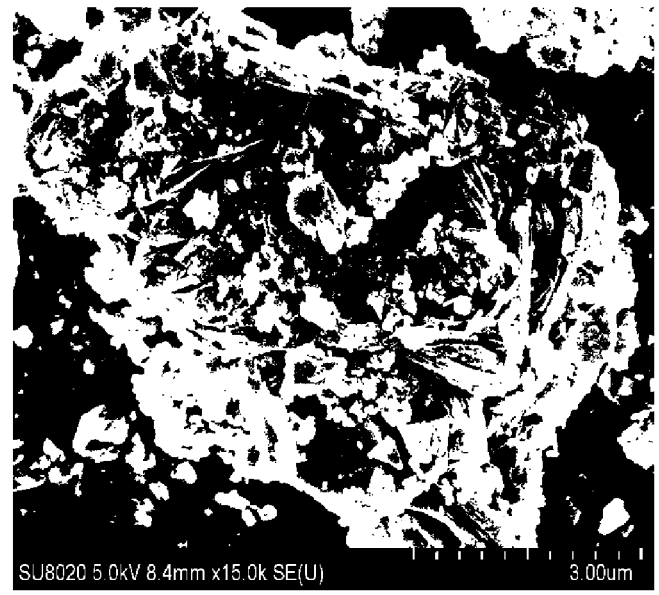
FIG. 2 is a scanning electron micrograph of an activated vanadyl phosphate catalyst obtained in step (4) in Example 1 of the present application.
Figure 3:
FIG. 3 is a scanning electron micrograph of a vanadyl phosphate catalyst precursor obtained in step (2) in Example 2 of the present application.
Figure 4:
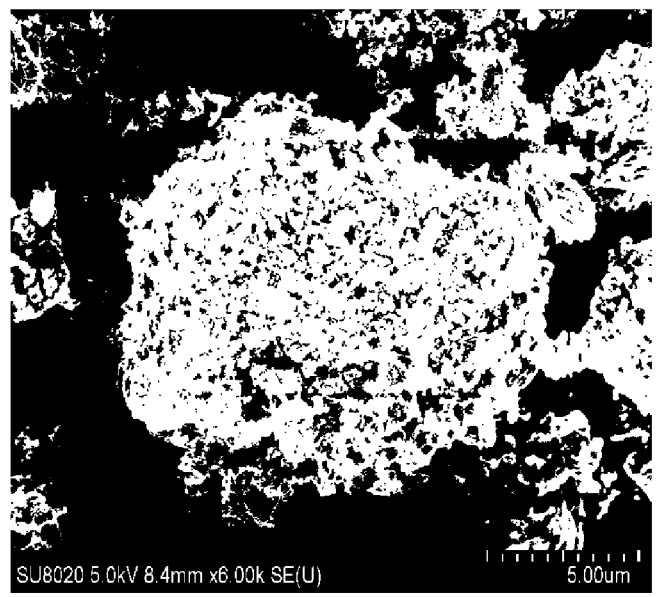
FIG. 4 is a scanning electron micrograph of an activated vanadyl phosphate catalyst obtained in step (4) in Example 2 of the present application.
Figure 5:
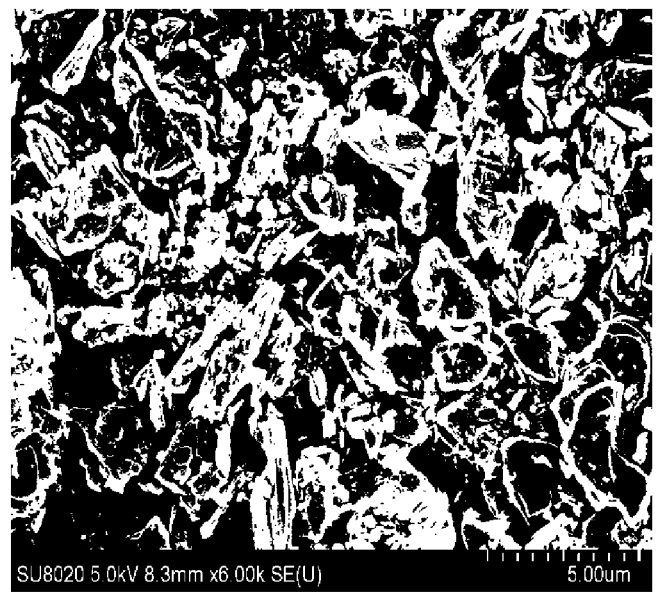
FIG. 5 is a scanning electron micrograph of a vanadyl phosphate catalyst precursor obtained in step (2) in Example 3 of the present application.
Figure 6:
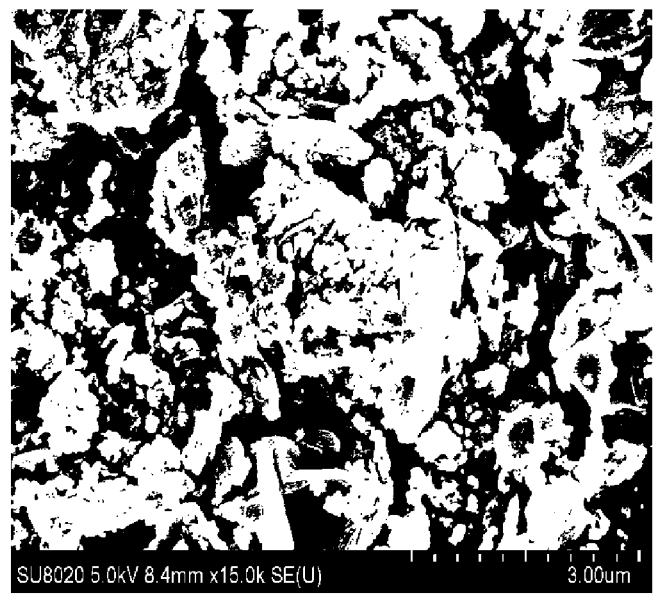
FIG. 6 is a scanning electron micrograph of an activated vanadyl phosphate catalyst obtained in step (4) in Example 3 of the present application.

FIG. 1 is a scanning electron micrograph of the vanadyl phosphate precursor obtained in step (2) in Example 1; FIG. 2 is a scanning electron micrograph of the activated vanadyl phosphate catalyst obtained in step (4) in Example 1; FIG. 3 is a scanning electron micrograph of the vanadyl phosphate catalyst precursor obtained in step (2) in Example 2; FIG. 4 is a scanning electron micrograph of the activated vanadyl phosphate catalyst obtained in step (4) in Example 2; FIG. 5 is a scanning electron micrograph of the vanadyl phosphate catalyst precursor obtained in step (2) in Example 3; and FIG. 6 is a scanning electron micrograph of the activated vanadyl phosphate catalyst obtained in step (4) in Example 3.

It can be seen from FIGS. 1 to 6 that the vanadyl phosphate catalyst precursor enhanced by the deep eutectic solvent becomes more dispersed, and has a larger sheet thickness and a larger specific surface area; and the improved catalyst, after being activated, has relatively stable structure and is not easy to collapse.

TABLE 1

| Catalyst precursor | $I_{(001)}/I_{(130)}$ | Half-peak Width (001) (Å) | Crystal Size (001) (nm) |
| --- | --- | --- | --- |
| Comparative example 1 | 51.2 | 0.396 | 20.9 |
| Example 1 | 68.5 | 0.214 | 42.5 |
| Example 2 | 71.5 | 0.251 | 34.8 |
| Example 3 | 82.6 | 0.247 | 35.4 |

TABLE 2

| Activated Catalyst | $I_{(020)}/I_{(204)}$ | Half-peak Width (020) (Å) | Grain Size (020) (nm) |
| --- | --- | --- | --- |
| Comparative example 1 | 59.3 | 0.381 | 22.0 |
| Example 1 | 56.9 | 0.538 | 15.3 |
| Example 2 | 74.4 | 0.557 | 14.8 |
| Example 3 | 65.2 | 0.502 | 16.5 |

From the crystallographic data of the precursors in Table 1, it can be seen that the vanadyl phosphate catalysts in Examples 1 to 3, relative to the vanadyl phosphate catalyst prepared without adding the deep eutectic solvent in Comparative Example 1, have I(001)/I(130) improved to different degrees, which indicates that the addition of the deep eutectic solvent can induce the growth of a precursor (001) plane, and this crystal plane is a main crystal plane conversed into an active plane. From the crystallographic data of the activated catalysts in Table 2, it can be seen that the catalysts with the addition of the deep eutectic solvent have significantly increased I(020)/I(204) intensity, which proves that the deep eutectic solvent has an effect of inducing the growth of the active plane, and their grain sizes are significantly reduced, which is beneficial to expose more active sites. Especially in Example 2, the relative content of (020) plane is the highest. The exposure of (020) plane increases the activity of the vanadyl phosphate catalyst. While, in Comparative Example 1, the crystal size is large and the active plane has low crystallinity, which are the reasons why the catalyst in Comparative Example 1 has low activity and easily loses activity in a reaction of selective oxidation of n-butane to maleic anhydride.

The applicant has stated that although the detailed method of the present application is described through the examples described above, the present application is not limited to the detailed method described above, which means that implementation of the present application does not necessarily depend on the detailed method described above. It should be apparent to those skilled in the art that any improvements made to the present application, equivalent replacements of raw materials of the product of the present application, additions of adjuvant ingredients in the product of the present application, and selections of specific manners, etc., all fall within the protection scope and the disclosed scope of the present application.

What is claimed is:

1. A method for preparing a vanadyl phosphate catalyst, comprising:
    (1) mixing a vanadium source with a deep eutectic solvent and alcohol to obtain a mixture, and reacting the mixture;
    (2) mixing a reaction product obtained in step (1) with a phosphorus source, raising the temperature to a temperature higher than a melting point of the deep eutectic solvent, and continuing a reaction to obtain a vanadyl phosphate precursor; and
    (3) carrying out calcination to obtain the vanadyl phosphate catalyst;
    wherein the deep eutectic solvent is a deep eutectic solvent formed by choline chloride and an organic carboxylic acid; and
    the alcohol is benzyl alcohol or a mixture of $C_3$-$C_8$ monohydric alcohol and benzyl alcohol.

2. The method of claim 1, wherein the organic carboxylic acid comprises any one or a combination of at least two of malonic acid, oxalic acid, and tartaric acid.

3. The method of claim 2, wherein the $C_3$-$C_8$ monohydric alcohol is any one or a combination of at least two of propanol, isobutanol, n-butanol, pentanol, hexanol, heptanol, and octanol.

4. The method of claim 3, wherein the alcohol is a mixture of isobutanol and benzyl alcohol.

5. The method of claim 1, wherein when the alcohol is benzyl alcohol, a volume ratio of the deep eutectic solvent to benzyl alcohol is (0.15-0.25): 1; or
    when the alcohol is the mixture of $C_3$-$C_8$ monohydric alcohol and benzyl alcohol, a volume ratio of the deep eutectic solvent, $C_3$-$C_8$ monohydric alcohol, and benzyl alcohol is (0.15-0.25): (3-5): 1.

6. The method of claim 1, further comprising, in addition to the vanadium source, adding either or both of a metal oxide and a metal salt while adding the deep eutectic solvent.

7. The method of claim 6, wherein a metal element in the metal oxide or the metal salt is independently selected from any one or a combination of at least two of Fe, Cu, Co, Mn, Ni, Zr, Zn, Ce, and Mo.

8. The method of claim 7, wherein an atomic molar ratio of the metal element to a vanadium element in the vanadium source is 0.0005-0.035.

9. The method of claim 1, wherein a mass ratio of the vanadium source to the deep eutectic solvent is (50-10): 1;
in the mixture, the vanadium source has a concentration of 0.02 g/mL to 0.12 g/mL; and
a molar ratio of phosphorus in the phosphorus source to vanadium in the vanadium source is (0.8-1.5): 1.

10. The method of claim 1, wherein a manner for the mixing in step (1) is placing the vanadium source in a vessel, and then adding a mixed solution of the deep eutectic solvent and the alcohol.

11. The method of claim 1, wherein in step (3), a calcination atmosphere is a nitrogen atmosphere, a mixed atmosphere of n-butane and air, or a mixed atmosphere of n-butane, oxygen, and nitrogen.

12. The method of claim 1, comprising:
(1) placing vanadium pentoxide in a vessel and then adding a deep eutectic solvent, isobutanol, and benzyl alcohol to be mixed with vanadium pentoxide to obtain a mixture, reacting the mixture at 130° C. to 140° C. for 3 h to 5 h, and then cooling the reaction product to 30-80° C.;
(2) adding a phosphorus source to the vessel, raising the temperature to 100° C. to 200° C., continuing a reaction for 10 h to 24 h, filtering, washing, and drying the resultant to obtain a vanadyl phosphate precursor; and
(3) carrying out calcination at 350° C. to 550° C. for 10 h to 24 h in a nitrogen atmosphere, a mixed atmosphere of n-butane and air, or a mixed atmosphere of n-butane, oxygen, and nitrogen, to achieve in-situ activation so as to obtain the vanadyl phosphate catalyst;
wherein the deep eutectic solvent is a deep eutectic solvent formed by choline chloride and an organic carboxylic acid;
a mass ratio of vanadium pentoxide to the deep eutectic solvent is (20-30): 1;
a volume ratio of the deep eutectic solvent, isobutanol, and benzyl alcohol is (0.15-0.25): (3-5): 1;
in the mixture, vanadium pentoxide has a concentration of 0.02 g/mL to 0.12 g/mL; and
a molar ratio of phosphorus in the phosphorus source to vanadium in the vanadium source is (0.9-1.2): 1.

13. A vanadyl phosphate catalyst prepared by the method of claim 1.

14. A method for selective oxidation of n-butane to maleic anhydride, comprising:
reacting the vanadyl phosphate catalyst of claim 13 with n-butane under reaction conditions comprising a reaction temperature of 400° C. to 550° C., a pressure of 0.1 MPa to 0.3 MPa, a space velocity of a mixed gas of n-butane of 1000 $h^{-1}$ to 2500 $h^{-1}$, and an n-butane concentration of 1.3 wt % to 1.8 wt %.

15. The method of claim 1, wherein a temperature for the reaction in step (1) is 100° C. to 180° C.

16. The method of claim 15, wherein a duration for the reaction in step (1) is 2 h to 8 h.

17. The method of claim 1, wherein in step (2), the temperature is raised to 35° C. to 200° C. higher than the melting point of the deep eutectic solvent.

18. The method of claim 17, wherein in step (2), the reaction is continued for a duration of 10 h to 24 h.

19. The method of claim 11, wherein in the mixed atmosphere of n-butane and air, a volume ratio of n-butane to the air is (0.8-1.8): 100.

20. The method of claim 1, wherein a temperature for the calcination in step (3) is 350° C. to 550° C.

* * * * *